United States Patent
Cantiani et al.

(10) Patent No.: US 6,312,669 B1
(45) Date of Patent: Nov. 6, 2001

(54) BUCCODENTAL FORMULATION COMPRISING ESSENTIALLY AMORPHOUS CELLULOSE NANOFIBRILS

(75) Inventors: Robert Cantiani, Lyons; Claudie Willemin, Paris, both of (FR)

(73) Assignee: Rhodia Chimie, Boulogne Billancourt Cedex (FR)

(*) Notice: Subject to any disclaimer, the term of this patent is extended or adjusted under 35 U.S.C. 154(b) by 0 days.

(21) Appl. No.: 09/508,228

(22) PCT Filed: Sep. 3, 1998

(86) PCT No.: PCT/FR98/01888

§ 371 Date: May 16, 2000

§ 102(e) Date: May 16, 2000

(87) PCT Pub. No.: WO99/15141

PCT Pub. Date: Apr. 1, 1999

(30) Foreign Application Priority Data

Sep. 22, 1997 (FR) .................................................. 97 11767

(51) Int. Cl.[7] .............................. A61K 7/16; B32B 1/08; C08L 1/02; C09D 101/02

(52) U.S. Cl. ..................... 424/49; 106/162.8; 106/731; 106/805; 162/27; 162/76; 162/187; 426/658; 426/573; 514/781

(58) Field of Search ..................... 424/49–58; 514/781; 106/162.8

(56) References Cited

U.S. PATENT DOCUMENTS

| 4,481,076 | * | 11/1984 | Herrick ................................ 162/158 |
| 4,629,575 | * | 12/1986 | Weibel ............................... 252/8.551 |
| 4,659,388 | * | 4/1987 | Innami et al. .................... 106/163.1 |
| 5,415,804 | * | 5/1995 | Minami et al. ................... 252/363.5 |
| 5,964,983 | * | 10/1999 | Dinand et al. ......................... 162/27 |
| 6,106,913 | * | 8/2000 | Scardino et al. .................... 428/36.3 |
| 6,224,663 | * | 5/2001 | Cantiani et al. .................. 106/162.8 |
| 6,231,657 | * | 5/2001 | Cantiani et al. .................. 106/162.8 |

FOREIGN PATENT DOCUMENTS

| 0 198 094 | 10/1986 | (EP) ................................ A61K/7/16 |
| 0726 356 | 8/1996 | (EP) ................................ D21H/11/18 |
| WO 98 02486 | 1/1998 | (WO) .................................. C08L/1/02 |
| WO 98 02487 | 1/1998 | (WO) .................................. C08L/1/02 |

* cited by examiner

Primary Examiner—Shep K. Rose
(74) Attorney, Agent, or Firm—Jean-Louis Seugnet

(57) ABSTRACT

The invention concerns buccodental formulation characterized in that it comprises at least a thickening agent comprising cellulose nanofibrils, said cellulose nanofibrils being substantially amorphous, having a crystallinity index not more than 50%. The invention also concerns said cellulose nanofibrils as thickening agent and/or flavour enhancer in buccodental formulations.

14 Claims, No Drawings

BUCCODENTAL FORMULATION COMPRISING ESSENTIALLY AMORPHOUS CELLULOSE NANOFIBRILS

This application is an application under 35 U.S.C. Section 371 of International Application Number PCT/FR98/01888, filed on Sep. 03, 1998.

The present invention relates to the use of essentially amorphous cellulose nanofibrils in buccodental formulations, and to the formulations thus obtained.

More specifically, the present invention relates to a novel thickener for buccodental formulations, which has in particular better thermal and ionic stability than the conventional thickeners, without any adverse impact on the other advantages required.

Usually, buccodental formulations contain wetting agents such as glycerol, polyethylene glycol or sorbitol, inorganic abrasive agents such as amorphous silica, hydrated or unhydrated dicalcic phosphates, calcium carbonate, washing surfactants, active agents such as antibacterial agents, for instance chlorhexidine, fluorine derivatives, enzymes and sweeteners such as sodium saccharinate, as well as many other components which contribute more particularly towards giving the said formulations a specific appearance, a particular taste and/or specific properties.

Among all of these compounds, some are in a water-soluble form while others, on the other hand, are in a solid powder form. To formulate them as a homogeneous mixture, it is thus necessary also to incorporate into the formulation at least one auxiliary agent acting more particularly as a binder for these various compounds. In parallel with this function, this agent generally contributes towards giving the buccodental formulation adequate rheological behaviour for the application envisaged, and is directed in particular towards thickening it. As representative examples of these conventional thickeners for buccodental formulations, mention may be made of thickening silicas, alginates, polysaccharides such as natural gums, for instance carrageenans, xanthan and guar and most particularly cellulose derivatives such as carboxymethylcellulose and hydroxyethylcellulose.

In point of fact, the thickeners of cellulose derivative type currently available are not entirely satisfactory.

It is necessary to use large amounts of them, about 1% approximately, in order to obtain a suitable viscosity. Moreover, formulations containing them are subject to considerable variations in viscosity when faced with high temperatures, or comprise a high ionic charge.

Lastly, the formulations based on these cellulose derivatives are not entirely satisfactory in aesthetic terms. Thus, compositions such as toothpaste, thickened with these cellulose derivatives, do not behave well on the toothbrush.

The object of the present invention is, precisely, to propose a novel thickener which is free of the abovementioned drawbacks but which has, on the other hand, advantageous rheological behaviour.

The Applicant has thus demonstrated that cellulose nanofibrils, that are essentially amorphous and advantageously obtained from primary walls, advantageously satisfy these two imperatives. Unexpectedly, cellulose fibres of this type show good compatibility with regard to the other components present in buccodental compositions.

In general, native cellulose is always in a fibrillar form. Its fibrils are well-known materials which have, in particular, already been proposed for modifying the texture of media into which they are introduced. In the case of fluid media, they modify their viscosities or even their rheological profiles.

Cellulose fibrils can be of diverse origin, for example of plant, bacterial, animal, fungal or amoebic origin.

Cellulose fibrils are usually strongly self-associated in the walls or the fibres. Secondary walls, which are mainly found in wood, are distinct from primary walls, a typical example of which is parenchyma. Examples of parenchyma consist of sugarbeet pulp, citrus fruits (lemons, oranges and grapefruit) and most fruit and vegetables.

In the secondary walls, these fibrils are organized in the form of highly oriented sheets thus forming an indissociable fibre. They are conventionally in the form of aggregates from a few tens of nanonetres to a few micrometres. These aggregates consist of elementary microfibrils which cannot be disentangled, during their homogenization, without resulting in breaking them.

In the context of the present invention, the cellulose fibrils considered are cellulose nanofibrils, CNF, preferably obtained from cells with primary walls.

In contrast with the cellulose microfibrils from secondary walls discussed above, they have a diameter of not more than a few nanometres and have the appearance of filaments. Advantageously, it is possible to disentangle these cellulose nanofibrils from primary walls during homogenization steps.

The main subject of the present invention is thus a buccodental formulation, characterized in that it comprises at least one thickener comprising cellulose nanofibrils, the said cellulose nanofibrils being essentially amorphous and having a degree of crystallinity of less than or equal to 50 %.

In the preferred variant of the invention, the cellulose nanofibrils are obtained from cells preferably consisting of at least about 80% primary walls. Preferably, the amount of primary walls is at least 85% by weight.

The nanofibrils will, in this case, have at least 80% of cells with primary walls.

They preferably have a section of between about 2 and about 10 nm. More preferably, this is between about 2 and about 4 nm.

In the context of the invention, the nanofibrils considered are so-called essentially amorphous nanofibrils, in contrast with so-called crystalline fibrils.

The term essentially amorphous is understood to define nanofibrils whose degree of crystallinity is less than or equal to 50%. According to a specific variant of the present invention, this degree of crystallinity is between 15% and 10% and more preferably less than 50%.

These essentially amorphous cellulose nanofibrils are particularly advantageous with regard to crystalline microfibrils, in the sense that they are dispersible in aqueous media, they give very specific rheological properties of rheofluidifying type and they are stable, either thermally or in media containing high ionic charges. In this regard, the essentially amorphous nanofibrils according to the invention advantageously give excellent viscosity to the formulations incorporating them and do so for a low concentration, of about 0.15% by weight, as against 1% for standard cellulose derivatives.

This good efficacy shown, at low dose, by the cellulose nanofibrils is in fact a consequence of their excellent rheological behaviour in terms of viscosity and rheofluidifying power.

The cellulose nanofibrils used according to the invention moreover show an ability to reinforce the flavours present in the buccodental formulations into which they are introduced. The sensory perception of the flavour by the user is accentuated.

According to a preferred mode of the invention, the cellulose nanofibrils forming part of the formulations claimed are laden at the surface with carboxylic acids and with acidic polysaccharides, alone or as a mixture.

The term carboxylic acids is understood to refer to simple carboxylic acids, as well as salts thereof. These acids are preferably chosen from uronic acids and are more particularly galacturonic acid and/or glucuronic acid.

As acidic polysaccharides, mention may be made of pectins including, more particularly, polygalacturonic acids. These acidic polysaccharides can be present as a mixture with hemicelluloses.

In fact, these surface-laden nanofibrils do not result from a simple mixing between the said nanofibrils and the acids and polysaccharides. Rather, it is a close combination between these two types of compounds derived directly From the process used to prepare the nanofibrils. The reason for this is that this preparation process can be such that the acids and polysaccharides are not totally separated from the fibres but remain at the surface of these fibres, thus giving them very specific properties. It is important to emphasize that these same properties will not be reproduced if the process subsequently continues with a complete separation of the nanofibrils from these acids and/or polysaccharides, followed by addition of the latter agents to the nanofibrils thus obtained.

The cellulose nanofibrils obtained after processes of this type are conventionally in the form of aqueous suspensions whose solids content is from about 1 to 10% by weight approximately. In this case, they are incorporated just as they are or in a dilute form in the formulations claimed.

In general, the nanofibrils are present in the buccodental formulations claimed in a proportion of 0.1 to 0.4%, and preferably from 0.15 to 0.3%, by weight.

According to a specific embodiment of the present invention, the essentially amorphous cellulose nanofibrils are present therein in a form combined with an additive. This additive is in fact an agent which allows the cellulose nanofibrils to be formulated in a solid, redispersible form.

To this end, it is advantageous to combine the cellulose nanofibrils with at least one polyhydroxylated organic compound (polyOH). This combination, carried out during the process for the preparation of the cellulose nanofibrils, has the advantage of allowing the said nanofibrils to be shaped in a dry, redispersible form. Needless to say, this has potential value with regard to the preparation of the corresponding buccodental formulations.

The polyhydroxylated organic compound (polyOH) is preferably chosen from carbohydrates and derivatives thereof, and polyalcohols. As representative examples of these carbohydrates, mention may be made most particularly of linear or cyclic $C_3$ or $C_6$, and preferably $C_5$ or $C_6$, monosaccharides such as fructose, mannose, galactose, talose, gulose, allose, altrose, idose, arabinose, xylose, lyxose and ribose, oligosaccharides such as maltose and lactose, polysaccharides such as starch, cellulose, xanthan gum and guar and fatty derivatives thereof such as sucroesters of fatty acids, carbohydrate alcohols such as sorbitol or mannitol, carbohydrate acids such as gluconic acid, uronic acid or galacturonic acid, as well as salts thereof, and carbohydrate ethers such as cellulose methyl, ethyl, carboxymethyl, hydroxyethyl and hydroxypropyl ethers.

As regards the polyalcohols, they can be, in particular, glycerol, pentaerythritol, propylene glycol, ethylene glycol and/or polyvinyl alcohols.

In the specific case of carbohydrates and derivatives thereof, which can be used, together with the essentially amorphous cellulose nanofibrils, mention may be made more particularly of carboxylated celluloses and preferably carboxymethyl cellulose, also denoted as CMC.

Cellulose is a polymer consisting of glucose monomer units. The carboxyl group is introduced therein in a manner which is known per se, by reacting chloroacetic acid with cellulose. Its degree of substitution thus corresponds to the number of carboxymethyl groups per glucose unit. The theoretical maximum degree is 3. These carboxylated celluloses are said to have a high degree of substitution for a value greater than 0.95 and a low degree of substitution for a value less than the latter. As regards this degree of polymerization, it varies over a wide range.

Thus, carboxymethyl celluloses of high masses are suitable, the content of carboxylated cellulose selected then being less than or equal to 30% by weight, or carboxymethyl celluloses of low masses are suitable, the carboxylated cellulose content being, in this case, more particularly between 10 and 30% by weight.

For an identical mass, it moreover turns out to be possible to further reduce the proportion thereof relative to the nanofibrils, by favouring the choice of a carboxymethyl cellulose with a high degree of substitution.

Such cellulose and carboxylated cellulose nanofibril mixtures are described in particular in the International patent applications PCT/FR 97/01290, published under No. WO 98/02486, and PCT/FR 97/01291 published under No. WO 98/102487.

Preferably, this polyhydroxylated organic compound (polyOH) is chosen from carboxymethyl-cellulose, xanthan gum, guars and sorbitol, and mixtures thereof.

The buccodental formulation claimed preferably comprises the polyhydroxylated compound(s) and the cellulose nanofibrils in a (polyOH)/[(polyOH)+(CNF)] weight ratio of less than or equal to 50% and preferably less than or equal to 30%.

According to a preferred mode of the invention, the buccodental formulation comprises cellulose nanofibrils in a form combined with carboxymethylcellulose (CMC) with a high degree of substitution, in a (CMC)/[(CMC)+(CNF)] weight ratio of less than or equal to 20%.

Another polyhydroxylated derivative, for example sorbitol, can also be combined with the CMC. In this specific case, the (CMC)/[total (polyOH)+(CNF)] weight ratio is thus significantly reduced.

The redispersible solid cellulose nanofibril composition can contain, besides the polyhydroxylated organic compound(s) defined above, at least one co-additive chosen from:

compounds of formula (R1R2N)COA, in which R1 and R2, which may be identical or different, represent hydrogen or a C1–C10 preferably C1–C5, alkyl radical, A represents hydrogen, a C1–C10, preferably C1–C5, alkyl radical, or the group $R'^1R'^2N$ with $R'^1$ and $R'^2$, which may be identical or different, representing hydrogen or a $C_1$–$C_{10}$, preferably $C_1$–$C_5$, alkyl radical, and preferably anionic, nonionic or amphoteric surfactants, it being possible for these co-additives to be used alone or as a mixture.

It should be noted that the use of these co-additives allows, in combination with the additive such as, for example, carboxymethylcellulose, reinforcement of the rheofluidifying profile of the cellulose nanofibrils, after redispersion.

As regards the compounds of the type $(R^1R^2N)COA$, it is preferred to use compounds comprising two amide functions. Urea is preferably used as co-additive.

As illustrations of amphoteric surfactants, mention may be made, without any limitation being implied, of amphoteric derivatives of alkylpolyamines, alkylbetaines, alkyldimethylbetaines, alkylamidopropylbetaines, alkylamidopropyldimethylbetaines, alkyltrimethylsulphobetaines, imidazoline derivatives such as alkyl amphoacetates, alkyl amphodiacetates, alkyl amphopropionates, alkyl amphodipropionates, alkylsultaines or alkylamidopropylhydroxysultaines, condensation products of fatty acids and of protein hydrolysates, it being possible for these compounds to be used alone or as a mixture. The Miranol and Mirataine product ranges may be suitable in particular for carrying out the present invention.

The nonionic or anionic surfactants which are suitable for the invention are, for example, sodium lauryl sulphate and alkylglucosides.

When the cellulose nanofibrils used according to the invention are combined with one or more polyhydroxylated compounds and, where appropriate, co-additive(s) mentioned above, the proportion of polyhydroxylated compound (s) and co-additive(s) is less than or equal to 30% by weight relative to the weight of nanofibrils, polyhydroxylated compound(s) and co-additive(s).

According to a specific embodiment of the invention, these solid, redispersible essentially amorphous cellulose nanofibril compositions comprise cellulose carboxylated to a high degree of substitution and, as co-additive, at least one compound chosen from surfactants.

The buccodental formulations according to the invention, incorporating cellulose nanofibrils in a solid, redispersible or non-redispersible form, i.e. mixed with at least one additive and, where appropriate, a co-additive, also comprise the other standard components of the intended application.

Thus, the essentially amorphous cellulose nanofibrils, preferably laden with acids, and combined, where appropriate, with a polyhydroxylated compound and optionally with a co-additive, are present in the formulation claimed as a mixture with at least one wetting agent, insoluble inorganic abrasive agents, other thickeners and various conventional components.

Among the wetting agents which can be used, mention may be made, for example, of glycerol, sorbitol, polyethylene glycols, polypropylene glycols, lactitol and xylitol, or mixtures thereof. This wetting agent can represent from about 2 to 85%, preferably from about 3 to 55%, by weight of the said buccodental formulation, expressed as solids content.

As abrasive agents, mention may be made in particular of amorphous silica, calcium carbonate, hydrated alumina, bentonite, aluminium silicate, zirconium silicate and sodium, potassium, calcium and magnesium metaphosphates and phosphates. These abrasive powders can constitute from about 5 to 50% by weight of the buccodental formulation.

Among the auxiliary thickeners, mention may be made most particularly of thickening silicas in an amount of about 1 to 15% by weight of the said composition, carrageenans, cellulose derivatives, gums such as xanthan gum, guar gum and alginates, in an amount which can range up to 5% by weight of the said formulation.

Lastly, the buccodental formulation can also contain washing surfactants such as those defined above as co-additives, detergents, dyes, antibacterial agents, fluoro derivatives, opacifiers, flavourings, sweeteners, antitartar agents, anti-plaque agents, bleaching agents, sodium bicarbonate, antiseptics, enzymes, natural extracts (camomile, thyme, etc.) etc.

The buccodental formulation generally contains 5 to 60% water.

It is clear that the choice of these so-called conventional compounds and the determination of their respective amounts are directly linked to the type of formulation envisaged, i.e. paste, gel or water for brushing the teeth. In the specific case of toothpastes, the concentration of mineral fillers will, for example, be favoured. These adjustments in fact fall within the context of operations that are routine to those skilled in the art.

For the purposes of the present invention, the term buccodental formulation is understood to cover any formulation of dental paste, liquid or gel type, as well as brushing solutions or sprays.

The nanofibrils forming part of the formulations according to the invention can be obtained from various processes already described in the literature.

Reference may be made in particular to the process described in European patent application EP-A-726,356.

The treatment therein is carried out on the pulp of plants with primary walls, i.e. wet, dehydrated pulp stored in silos or partially depectinized, such as, for example, pulp from beetroot after it has undergone a prior sucrose extraction step, according to the methods known in the art. More specifically, it comprises a first acidic or basic extraction, after which a first solid residue is recovered, optionally followed by a second extraction, carried out under alkaline conditions, on the first solid residue, recovery of a second solid residue, washing and then bleaching of the two combined residues of cellulosic material, dilution of the third solid residue obtained after the bleaching step, followed by dilution of the resulting suspension, so as to obtain a solids content of between 2 and 10% by weight, and finally a homogenization step comprising at least one cycle of the dilute suspension.

More specifically, the homogenization step corresponds to a mixing or grinding operation or any mechanical high-shear operation, followed by one or more passages of the cell suspension through an orifice of small diameter, subjecting the suspension to a pressure drop of at least 20 mPa and to a high-speed shear action, followed by a high-speed deceleration impact. Homogenization of the cellulosic suspension is obtained by a number of passages which can range between 1 and 20, preferably between 2 and 5, until a stable suspension is obtained.

As regards the detailed procedure of each of the steps of this treatment, reference will be made to the description of the application identified above.

The process which has just been described makes it possible to obtain nanofibrils which conserve carboxylic acids and/or polysaccharides at their surface.

When the cellulose nanofibrils are used in the compositions claimed, in a form supplemented with a polyhydroxylated compound such as, for example, carboxylated cellulose, this added compound can be introduced into the preparation procedure described above, either before carrying out the homogenization step or after a homogenization cycle has been carried out.

It should be noted that this process variant is described in International patent application PCT/FR 97/01291 published under the number WO 98/02487, to which reference may be made, if necessary.

The process for preparing cellulose nanofibrils supplemented with polyhydroxylated compound(s) consists, in a first step, in adding to the nanofibril suspension, which has optionally undergone at least one homogenization cycle, at least some of the polyhydroxylated compound considered and optionally some of the co-additive(s). Next, in a second step, a step of drying of the suspension thus supplemented is carried out.

Example 1 presented below illustrates one specific mode for preparing cellulose nanofibrils supplemented with carboxymethylcellulose.

In point of fact, the addition of at least some of the polyhydroxylated compound and optionally some of the co-additive(s) can be carried out according to three variants:

either after the homogenization step and, according to a preferred mode, after this material has undergone at least one concentration step, or to the suspension obtained after the homogenization step, before this suspension has undergone at least one concentration step, or alternatively before or during the homogenization step, the pulp then having undergone at least one cycle of the homogenization step.

The concentration step(s) can be carried out by any conventional means until a solids content of about 35% by weight is obtained. More particularly, the solids content is between 5 and 25% by weight.

Prior to the actual drying step, it may be advantageous to carry out a shaping operation, i.e. by extrusion or granulation, on the suspension which has been concentrated. The temperature of the drying step is, needless to say, selected so as to limit any degradation of the carboxylic acids, of the polysaccharide acids, of the hemicelluloses and/or of the polyhydroxylated compounds and co-additives. It is more particularly between 30 and 80° C., preferably between 30 and 60° C.

The drying step, carried out by conventional means, is carried out so as to maintain a minimum of 3% by weight of water relative to the weight of the solid obtained. More particularly, the weight of water maintained is between 10 and 30% by weight. Such an implementation makes it possible not to exceed the threshold beyond which redispersion of the nanofibrils can no longer be complete.

Advantageously, the cellulose nanofibril suspension obtained by redispersion in water of the mixture, obtained according to the process described above, has a viscosity level corresponding to at least 50%, for a shear rate of at least $1 \text{ s}^{-1}$, of the viscosity level of a cellulose nanofibril suspension which has not undergone a drying step and comprises neither any polyhydroxylated compound nor any co-additives.

The subject of the present invention is also the use of the essentially amorphous cellulose nanofibrils having a degree of crystallinity of less than or equal to 50%, as defined above, combined, where appropriate, with at least one polyhydroxylated organic compound (polyOH) and optionally with a co-additive as defined above, as a thickener and/or as a flavour enhancer in buccodental formulations.

The invention is also directed towards a process for thickening a buccodental formulation, characterized in that it comprises the addition, to the said formulation, of essentially amorphous cellulose nanofibrils having a degree of crystallinity of less than or equal to 50%, and, where appropriate, of at least one polyhydroxylated compound and optionally a co-additive as defined above.

The examples given below are presented merely by way of non-limiting illustration of the present invention.

EXAMPLE 1
Preparation of a Mixture Based on Cellulose Nanofibrils and on Carboxymethylcellulose with a High Degree of Substitution A carboxymethylcellulose, with a high degree of substitution equal to 1.2 (CMC Blanose 12M8P from Aqualon) is dissolved in distilled water.

The solution is then added to the stock dispersion of nanofibrils at a concentration of 2.3% cellulose nanofibrils and prehomogenized in an Ultra-Turrax machine at 14,000 rpm (1 min per 100 g of dispersion). The whole is stirred with a deflocculating paddle at 1000 rpm for 30 min.

The amount of carboxymethylcellulose added is 15% by weight, relative to the weight of cellulose nanofibrils and carboxymethylcellulose.

The mixture is then poured into dishes, after which it is dried, i.e. in a ventilated oven at 40° C., to a solids content of 92%, controlled by assaying the water by the Karl-Fischer method.

The dried mixture is then ground, after which it is screened through a 500 μm sieve.

The powder obtained is redispersed at a proportion of 0.3% by weight of cellulose nanofibrils in distilled water. Stirring is carried out using a deflocculating paddle at 1000 rpm for 5 min or 30 min.

EXAMPLE 2
Preparation of Formulations in Accordance with the Invention and of Control Formulations Three formulations according to the invention are prepared, incorporating, respectively:

0.3% of essentially amorphous cellulose nanofibrils, expressed as solids: formulation CNF(I), 0.15% of essentially amorphous cellulose nanofibrils, expressed as solids: formulation CNF(II), or a solid mixture of cellulose nanofibrils/carboxymethylcellulose prepared according to Example 1, in the proportion of 0.2% of nanofibrils, expressed as solids: CNF/CMC formulation.

They are compared with two control formulations:

a formulation based on xanthan gum, incorporated at an active material concentration of 0.8%, and a formulation simply incorporating the carboxymethylcellulose at an active material concentration of 1.2%.

Table 1 below summarizes the nature of the other components in each of the formulations tested, as well as their respective amounts.

TABLE 1

| INGREDIENT | Control xanthan gum | Control CMC | CNF I | CNF II | CNF/CMC |
|---|---|---|---|---|---|
| Rhodicare S ® | 0.8 | | | | |
| Blanose 12M8P ® | | 1.2 | | | |
| CNF dispersion at 2.3% | | | 13.00 | 6.5 | |
| CNF/CMC mixture | | | | | 0.2 |
| 70% sorbitol (Neosorb 70/70 ®) | 40.9 | 40.9 | 60.64 | 67.14 | 67.14 |
| Sodium monofluorophosphate (Na MFP) | 0.76 | 0.76 | 0.76 | 0.76 | 0.76 |
| Sodium saccharinate | 0.2 | 0.2 | 0.2 | 0.2 | 0.2 |
| Sodium benzoate | 0.2 | 0.2 | 0.2 | 0.2 | 0.2 |
| Tixosil 73 | 10.0 | 10.0 | 10.0 | 10.0 | 10.0 |
| Tixosil 43 | 10.0 | 10.0 | 10.0 | 10.0 | 10.0 |
| TiO$_2$ | 1.0 | 1.0 | 1.0 | 1.0 | 1.0 |
| Sodium lauryl sulphate (30%) | 4.2 | 4.2 | 4.2 | 4.2 | 4.2 |
| Peppermint flavouring | 1.0 | 1.0 | 1.0 | 1.0 | 1.0 |
| water | qs 100 | qs 100 | 0 | 0 | 6.3 |

1) Preparation of the control formulations

Sodium salts are dissolved in aqueous medium and the solution thus obtained is mixed with Neosorb® 70/70. Either xanthan gum (Rhodicare S®) or carboxymethylcellulose (Blanose 12M8P®) is then dispersed in the mixture, using a Rayneri-type homogenizer, for one minute at 600 rpm, after which hydration is carried out (for 15 minutes at 2000 rpm) The whole mixture is then transferred into a Guedo®-type grinder and left to stand for 30 minutes. The silicas and the titanium oxide are then added with stirring. After stirring for 10 minutes, the mixture is cooled and placed under vacuum. This entire stirring-cooling operation is carried out over one hour. The stirring speed is then reduced and the surfactant and the flavouring are added, under vacuum. The resultant mixture is mixed for 5 minutes, after which the vacuum is broken, the mill is emptied and the paste thus obtained is packaged.

2) Preparation of the formulations according to the invention a) Preparation of the CNF(I) formulation According to a first procedure, a cellulose nanofibril dispersion at 2.3% by weight of CNF is dispersed in a water/Neosorb® 70/70 mixture so as to adjust it to a final concentration of 0.3% CNF, with an Ultra-Turrax®-type grinder for 3 minutes and at a speed of 14,000 rpm. This mixture is then transferred into the mill, in which no phase of leaving to stand is carried out. The silicas, the titanium oxide and the sodium salts are then added with stirring. After 10 minutes, this mixture is cooled and placed under vacuum, the operation being carried out in a total time of 1 hour.

The remainder of the process is carried out in accordance with the process described for the production of the control formulations.

b) Preparation of the CNF(II) formulation

According to a second procedure, a dispersion of cellulose nanofibrils at 2.3% by weight of CNF is dispersed in a Rayneri®-type homogenizer in order to obtain a concentration of 0.15% CNF, in a water/Neosorb® 70/70 mixture at a speed of 600 rpm, after which hydration is subsequently carried out for 30 minutes at a speed of 2000 rpm. All of this mixture is then transferred into a mill, in which no phase of leaving to stand is carried out. The rest of the test is then carried out in accordance with the procedure described for the preparation of the CNF(I) formulation.

c) Preparation of the CNF-CMC formulation

In this case, the CNF-CMC mixture containing 15% of CMC with a high degree of substitution, prepared according to Example 1, is used. This solid mixture, with a solids content of 92%, is dispersed in a proportion of 0.16% by weight using a Rayneri®-type homogenizer in a water-Neosorb® 70/70 mixture at 600 rpm, after which hydration is carried out for 30 minutes at 10,000 rpm. This mixture is then transferred into the mill, in which no phase of leaving to stand is carried out. The rest of the test is carried out in accordance with the procedure described for the preparations of the above two formulations.

EXAMPLE 3

Evaluation of the Properties of the Toothpastes Formulated According to Example 1

This evaluation is carried out after maturation for one week. The criteria selected are:

the appearance evaluated visually; it is graded from 0 (poor appearance) to ++ (good appearance), and the consistency, measured using a Brookfield RV 8®-type viscometre fitted with a helipath baseplate, at 0.5 rpm.

The results observed are featured in Table 2 below.

TABLE 2

| Composition | Appearance | Consistency (Pa·s) |
| --- | --- | --- |
| Control xanthan gum | ++ | 123 |
| Control CMC | ++ | 145 |
| CNF(I) | ++ | 385 |
| CNF(II) | ++ | 320 |
| CNF/CMC | ++ | 320 |

By examining these results, it emerges that the cellulose nanofibrils give toothpastes which have advantageous consistencies and do so more particularly for a concentration of about 0.15% by weight.

EXAMPLE 4

Evaluation of the Flavour-enhancing Effect of the Cellulose Nanofibrils

This evaluation is carried out by sensory analysis performed on 10 individuals, by testing a buccodental formulation in accordance with the invention against a control buccodental formulation containing no cellulose nanofibrils.

The compositions of each of the formulations tested are identified below.

The CNF composition used comprises 70% by weight of pure CNF, 5% by weight of CMC (Blanose 7HXF) and 25% by weight of sorbitol. This composition is referred to as CNF/CMC/sorbitol in the buccodental formulation tested below.

| Buccodental formulation with CNF | |
| --- | --- |
| Product | % w/w |
| CNF/CMC/sorbitol | 0.25 |
| Neosorb ® 70/70 | 67.09 |
| Sodium monofluorophosphate | 0.76 |
| Sodium saccharinate | 0.2 |
| Sodium benzoate | 0.2 |
| Tixosil 73 | 10.0 |
| Tixosil 43 | 10.0 |
| $TiO_2$ | 1.0 |
| Sodium lauryl sulphate Sipon LCS 98 (30% solution) | 4.2 |
| Herbal flavouring ® from the company Mane | 1.0 |
| Water qs | 100 |

| Buccodental formulation with CMC | |
| --- | --- |
| Product | % w/w |
| Blanose 7HXF | 0.4 |
| Neosorb ® 70/70 | 66.87 |
| Sodium monofluorophosphate | 0.76 |
| Sodium saccharinate | 0.2 |
| Sodium benzoate | 0.2 |
| Tixosil 73 | 10.0 |
| Tixosil 43 | 10.0 |
| $TiO_2$ | 1.0 |
| Sodium lauryl sulphate Sipon LCS 98 (30% solution) | 4.2 |
| Herbal flavouring ® from the company Mane | 1.0 |
| Water qs | 100 |

The formulation according to the invention is obtained by dispersing and hydrating the CNFs in Neosorb® 70/70 for 10 min with an Ultra-Turrax machine at 24,000 rpm and using a deflocculating paddle for 30 min at 2000 rpm, by immediate transfer of the mixture into a mill. The silicas, the sodium salts and the titanium oxide are then introduced therein with stirring. The mixture is stirred for one hour, 50 minutes of which are under vacuum, and with cooling to 23° C. The surfactant and the flavouring are then introduced with stirring and under vacuum. This mixture is stirred for 5 min, after which the mill is emptied and its contents are recovered.

The control formulation is obtained by dispersing and hydrating the CMC in the Neosorb® 70/70 using a deflocculating paddle for 15 min at 2000 rpm. After this operation, the mixture is transferred into a mill and the process is performed according to the procedure described above to obtain the control formulation.

The criteria selected for this evaluation and the results obtained are given in Table III below. Each criterion is graded from 0 (poor behaviour) to +++ (good behaviour).

TABLE 3

|  | CNF formulation | Control formulation |
| --- | --- | --- |
| Perception of the flavouring | +++ | +++ |
| Intensity of the flavouring on brushing | +++ | ++ |
| Intensity of the flavouring after brushing | +++ | ++ |
| Reminiscence in the mouth after 10 minutes | ++ | <+ |

What is claimed is:

1. A buccodental formulation, comprising at least one thickener comprising cellulose nanofibrils, said cellulose nanofibrils being essentially amorphous and having a degree of crystallinity of less than or equal to 50%, said cellulose nanofibrils being present therein in a form combined with at least one polyhydroxylated organic compound (polyOH) with a (polyOH)/[(polyOH)+(CNF)] weight ratio less than or equal to 30%.

2. A buccodental formulation according to claim 1, wherein the degree of crystallinity is between 15 and 50%.

3. A buccodental formulation according to claims 1, wherein the cellulose nanofibrils are obtained from cells having at least about 80% primary walls.

4. A buccodental formulation according to claim 3, wherein the amount of primary walls is at least 85% by weight.

5. A buccodental formulation according to any one of claims 1, comprising about 0.1 to 0.4% by weight of said cellulose nanofibrils.

6. A buccodental formulation according to claim 5, comprising about 0.15 to 0.3% by weight of said cellulose nanofibrils.

7. A buccodental formulation according to claim 1, wherein the cellulose nanofibrils are also laden at the surface with carboxylic acids, or acidic polysaccharides.

8. A buccodental formulation according to claim 1, wherein the polyhydroxylated organic compound (polyOH) is carbohydrates, carbohydrates derivatives, or polyalcohols.

9. A buccodental formulation according to claim 8, wherein the carbohydrates are C3 to C6 monosaccharides, oligosaccharides, polysaccharides, sucroesters of fatty acids, carbohydrate alcohols, carbohydrate acids or carbohydrate ethers.

10. A buccodental formulation according to claim 1, wherein the polyhydroxylated organic compound (polyOH) is carboxymethylcellulose, xanthan gum, guaror sorbitol.

11. A buccodental formulation according to claim 10, wherein the cellulose nanofibrils are further combined therein with carboxymethylcellulose (CMC) with a high degree of substitution, in a (CMC)/[(CMC)+(CNF)] weight ratio of less than or equal to 20%.

12. A buccodental formulation according to claim 11, wherein the cellulose nanofibrils therein are further combined with one or more co-additives which are:

compounds of formula (R1R2N)COA, wherein R1 and R2, which are identical or different, represent hydrogen or a C1–C10 alkyl radical, A represents hydrogen, a C1–C10 alkyl radical, or the group $R'^1R'^2N$ with $R'^1$ and $R'^2$, which are identical or different, representing hydrogen or a $C_1$–$C_{10}$, alkyl radical, nonionic surfactants, anionic surfactants, or amphoteric surfactants.

13. A buccodental formulation according to 12, wherein the content of polyhydroxylated compound and of optional co-additive is less than or equal to 30% by weight relative to the weight of nanofibrils, polyhydroxylated compound and co-additive.

14. A process for thickening a buccodental formulation comprising the step of adding a thickening amount of a thickener comprising cellulose nanofibrils, said cellulose nanofibrils being essentially amorphous and having a degree of crystallinity of less than or equal to 50%, said cellulose nanofibrils being present therein in a form combined with at least one polyhydroxylated organic compound (polyOH) with a (polyOH)/[(polyOH)+(CNF)] weight ratio less than or equal to 30%.

* * * * *